United States Patent [19]
Olmstead

[11] Patent Number: 4,755,166
[45] Date of Patent: Jul. 5, 1988

[54] MULTI-FINGERED TAMPON APPLICATOR COMBINATION

[75] Inventor: Paul E. Olmstead, Menasha, Wis.

[73] Assignee: Kimberly-Clark Corporation, Neenah, Wis.

[21] Appl. No.: 943,535

[22] Filed: Dec. 18, 1986

[51] Int. Cl.$^4$ .............................................. A61F 13/20
[52] U.S. Cl. ..................... 604/11; 604/286; 604/385 R; 604/904
[58] Field of Search ..................... 604/11–16, 604/286, 358, 363, 385.1, 904; 128/127, 130, 356; 221/312 A; 294/55.5

[56] References Cited

U.S. PATENT DOCUMENTS

| | | | |
|---|---|---|---|
| D. 263,503 | 3/1982 | Williams | D24/99 |
| 874,495 | 12/1907 | Gaterman | 128/356 |
| 2,146,574 | 2/1939 | Hay | 128/127 |
| 2,733,714 | 2/1956 | Haas | 128/263 |
| 2,877,767 | 3/1959 | Kramer | 604/11 |
| 3,765,417 | 10/1973 | Crockford | 128/263 |
| 3,885,563 | 5/1975 | Johnson et al. | 128/263 |
| 3,983,875 | 10/1976 | Truman | 128/285 |
| 4,148,317 | 4/1979 | Loyer | 128/263 |
| 4,676,773 | 6/1987 | Sheldon | 604/11 |

FOREIGN PATENT DOCUMENTS 0166106  6/1950  Austria .................. 604/11

*Primary Examiner*—Dalton L. Truluck
*Assistant Examiner*—Frank Wilkens
*Attorney, Agent, or Firm*—Paul A. Leipold

[57] ABSTRACT

The invention is generally accomplished by providing a tampon-applicator combination wherein the tampon is a generally elongated tampon having a series of grooves in the surface. An applicator is provided that has a handle and a series of prongs corresponding to the number of grooves in the tampon. The prongs are placed in the grooves of the tampon and hold the tampon for insertion into the vagina. The prongs do not resist withdrawal from the grooves when the applicator is removed from the vagina, leaving the tampon in place.

16 Claims, 2 Drawing Sheets

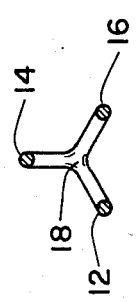
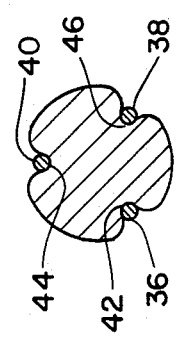
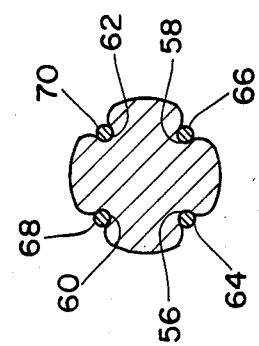
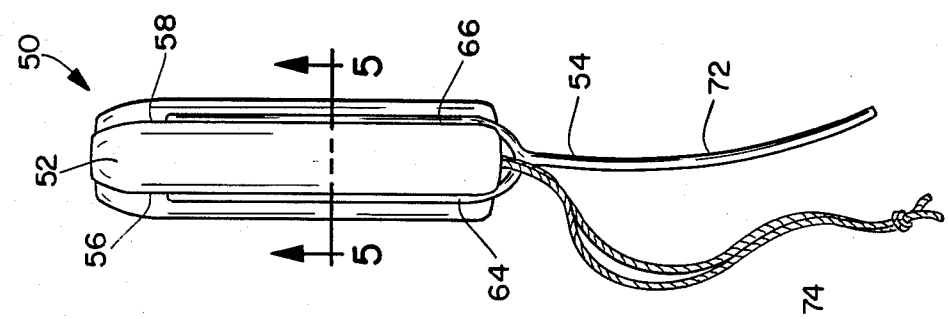
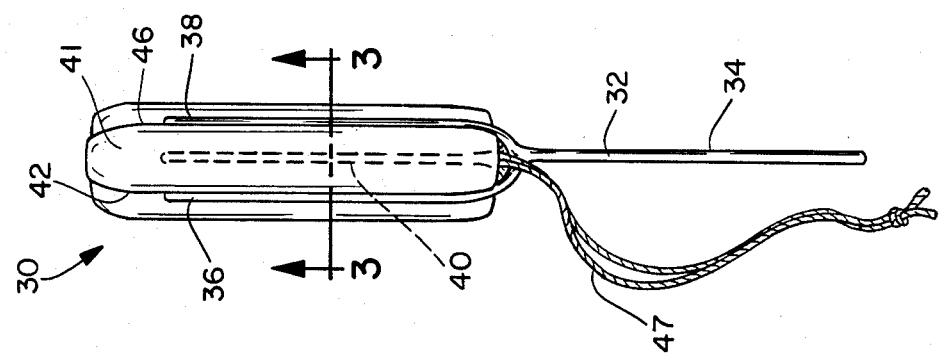
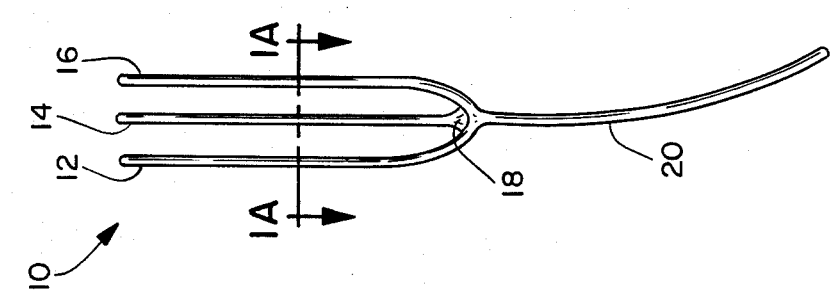

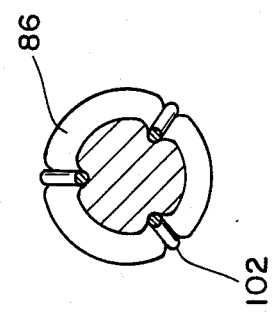
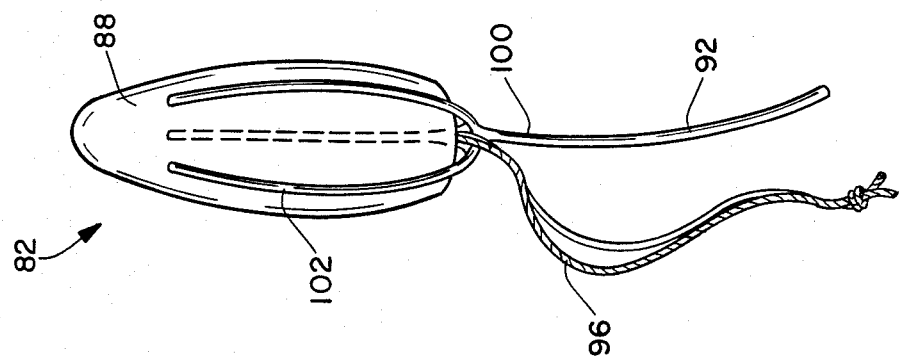
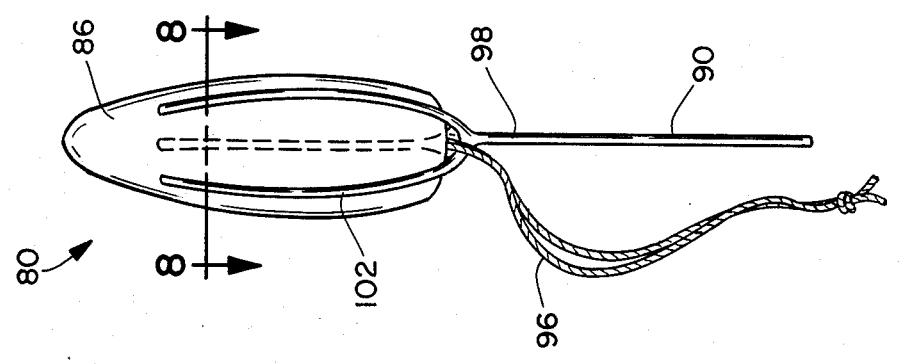

1

MULTI-FINGERED TAMPON APPLICATOR COMBINATION

TECHNICAL FIELD

This invention relates to a tampon applicator. It is particularly directed toward a tampon-applicator combination utilizing a multi-fingered stick that is adapted to grip the exterior of a tampon for insertion.

BACKGROUND ART

In the art there have been several methods of insertion of internally-applied catamenial tampons. One type which is on the market comprises a compressed round-nosed tampon having an inserter stick removably seated and frictionally held in a socket disposed in the rear portion of the tampon. Another type comprises a tube that houses the tampon pledget. The tube is inserted in the vagina, and the tampon is ejected from the tube. A third type of tampon utilizes a round-nosed tampon that is digitally inserted into the vagina. U.S. Pat. No. 3,765,417—Crockford illustrates a tube-type applicator for tampons. U.S. Pat. No. 3,983,875—Truman illustrates a stick-type applicator for tampons. In U.S. Pat. No. Des. 263,503—Williams, a tampon applicator having a scoop-shaped holding means on the end has been proposed.

There have been disadvantages to previous methods of tampon insertion. Digital insertion of tampons has been considered undesirable by many as their fingers may become soiled, and it may not be hygienically satisfactory. Tube-type applicators, while generally satisfactory, have the disadvantage that the tubes are of relatively complicated construction and add significantly to the cost of the tampons. Further, there may be pinching of tissue within the vagina involved in the ejection of the tampon and withdrawal of the tampon tube. A disadvantage of stick-type applicators with the stick in a hole within the rear of the tampon is that the tampons are required to be quite hard and rigid. Such tampons may not expand rapidly enough to prevent leakage around the tampon prior to its softening and becoming fully effective. Tube-type applicators allow use of softer tampons. Digitally-inserted tampons also are required to be somewhat harder than tube-type tampons.

There is a need for a tampon that has the simplicity, hygienic properties and low cost of the stick applicator tampon or digital tampon without the necessity for the hard tampon.

DISCLOSURE OF THE INVENTION

An object of this invention is to overcome disadvantages of prior tampon-applicator combinations.

A further object of the invention is to provide stick-type application of soft tampons.

A further object of the invention is to provide improved protection from leakage for tampon wearers.

These and other objects of the invention are generally accomplished by providing a tampon-applicator combination wherein the tampon is a generally elongated tampon having a series of grooves in the surface. The applicator has a handle and a series of prongs corresponding to the number of grooves in the tampon. The prongs are placed in the grooves of the tampon and hold the tampon for insertion into the vagina. The prongs do not resist withdrawal from the grooves when the applicator is removed from the vagina, leaving the tampon in place

BRIEF DESCRIPTION OF THE DRAWINGS

FIG. 1 is a plan view of the inserter of the invention.

FIG. 1A is a cross-sectional view on line 1A—1A of FIG. 1.

FIG. 2 is a view of the tampon-applicator combination of the invention.

FIG. 3 is a cross-section of FIG. 2 on line 3—3.

FIG. 4 is a view of a tampon-applicator combination of the invention having four prongs.

FIG. 6 is a view of a tampon-applicator combination of the invention with a tampon having oval cross-sections.

FIG. 7 is a view of a tampon-applicator combination of the invention with an oval tampon and a curved-handled applicator.

FIG. 8 is a view on cross-sectional line 8—8 of FIG. 6.

MODES FOR CARRYING OUT THE INVENTION

The tampon-applicator system of the invention has numerous advantages over prior practices. The tampon-applicator provides a means for insertion of a tampon that is low in cost. The applicator of the invention allows the use of a softer tampon than the conventional stick applicator. Further, the tampon is held securely in the applicator prior to insertion but nevertheless does not have a tendency to withdraw the tampon when the applicator is removed from the vagina. These and other advantages will be apparent from the detailed description below.

FIG. 1 illustrates a view of a tampon applicator 10 in accordance with the invention. As may be seen in FIG. 1a, the prongs 12, 14 and 16 are spaced generally equal distance from each other. The prongs 12, 14 and 16 join in area 18 and a curved handle 20 descends from the point of joinder 18.

FIG. 2 illustrates another embodiment of a tampon-applicator 30 of the invention. The applicator 32 has a straight handle 34 and is provided with three prongs 36, 38 and 40. The tampon 41 is provided with grooves 42, 44 and 46 into which the prongs 36, 38 and 40 are placed. When the tampon is inserted into the vagina, the walls of the vagina will grip the tampon 41 with enough force to allow removal of applicator 32 by withdrawal of the prongs 36, 38 and 40 from grooves 42, 44 and 46. The grooves or prongs may be lubricated to aid separation. After withdrawal of the applicator 32, the tampon withdrawal cord 47 may be utilized to remove the tampon after use.

FIG. 4 illustrates another alternate tampon-applicator 50 of the invention. The tampon 52 is provided with four grooves as more clearly illustrated in the cross-sectional view of FIG. 5 with four grooves 56, 58, 60 and 62. The applicator 54 is provided with four prongs 64, 66, 68 and 70. The applicator 54 has a curved handle 72. After use of the applicator 50 for placement of the tampon 52 into the vagina, the tampon may be withdrawn by cord 74 after use.

FIGS. 6 and 7 illustrate two other embodiments of the invention tampon-applicators 80 and 82. The tampon-applicators 80 and 82 are comprised of the somewhat egg-shaped rounded tampon pledgets 86 and 88. The embodiments of FIGS. 6 and 7 differ in that handle 90 of tampon-applicator 80 is straight while handle 92 of tampon-applicator 82 is curved. The tampons are provided with withdrawal cord 96, and each of the applicators 98 and 100 have three prongs 102.

As better illustrated, in the FIG. 8 cross-section of FIG. 6, the prongs 102 are somewhat arcuate and curve around the egg-shaped tampon 86. This serves to more securely hold the tampon against accidentally being disengaged from the holder 98 prior to use such as during unwrapping.

The applicator of the invention may be formed of any suitable material. Typical of such materials are plastics, metal and wood. A particularly preferred material is a moldable polymer such as polypropylene, polyethylene or polystyrene as these materials are flexible, have good hygienic properties and are low in cost. Composites of these materials also may be utilized. Also suitable would be composites of polymers with reinforcement materials such as fiberglass or metal.

The material forming the tampon may be any suitable tampon pledget material. The material may be selected from artificial and natural fibers, including cotton, polyester, cellulose acetate, nylon, polypropylene, rayon fibers and blends of these fibers. The tampon should be rigid enough to be suitable for insertion in the vagina without deformation. However, as it is held by the prongs of the applicator, it does not need to be as rigid as a stick tampon or digital tampon. The withdrawal cord utilized in the invention may be any suitable material such as cotton string, polymer strings, such as rayon and polyester, or polymer cords. Generally the withdrawal cord should not wick moisture to a great extent. The string may be wax treated to inhibit wicking. Further, the cord should be unobtrusive and comfortable. Preferred materials have been found to be cotton, rayon and polyester strings as they are low in cost.

While the invention has been described with utilization of menstrual absorbent tampons, it is also suitable for insertion of medicinal or contraceptive tampons into the vagina.

The handle of the applicator may extend any suitable distance so as to allow easy gripping of the applicator, as well as insertion into the vagina by a proper amount. Generally the handle would be about 4 to 6 inches long from the point below where the prongs come together. The handle further may be curved by any desired amount to aid in insertion and proper placement of the tampon.

The prongs of the applicator should be of sufficient length to grip the tampon. Generally a length of between one-half and three-fourths of the tampon length is preferred for secure grip and also easy release of the tampon. The prongs may be spaced such that they are expanded apart when the tampon is inserted in the applicator. The tendency of the prongs to return to their original spacing provides a gripping force on the tampon.

While the invention has been described with reference to specific preferred embodiments, it is within the invention to utilize other modifications and variations. For instance, the systems of the invention could also be utilized to place suppositories or to place packings into the nose or other body cavities to prevent bleeding. The invention is only intended to be limited by the breadth of the claims attached hereto.

We claim:

1. A tampon and inserter combination comprising an elongate compressed tampon, a withdrawal string attached to said tampon, at least three longitudinal grooves in said tampon and an inserter comprising at least three prongs resting in said grooves and an insertion handle joined to said prongs.

2. The combination of claim 1 wherein said handle is curved.

3. The combination of claim 1 wherein said inserter comprises three prongs.

4. The combination of claim 1 wherein said tampon has a rounded forward end.

5. The combination of claim 1 wherein said prongs are curved.

6. The combination of claim 1 wherein the depth of said grooves is substantially equal to the thickness of said prongs.

7. The combination of claim 1 wherein said prongs are arcuate and said tampon is of greatest thickness in its middle portion.

8. The combination of claim 1 wherein said prongs are spread when said tampon is inserted in said applicator.

9. A method of tampon insertion comprising providing an elongate tampon provided with at least three longitudinal grooves, an inserter having at least three prongs resting in said grooves and an insertion handle joined to said prongs, holding said handle, inserting said tampon and the forward portion of said inserter into the vagina and withdrawing said inserter.

10. The method of claim 9 wherein said handle is curved.

11. The method of claim 9 wherein said inserter comprises three prongs.

12. The method of claim 9 wherein said tampon has a rounded forward end.

13. The method of claim 9 wherein said prongs when resting in said grooves have their outer surface about even with the outer tampon surface.

14. The method of claim 9 wherein the depth of said grooves is substantially equal to the thickness of said prongs.

15. A device for insertion of articles into body cavities comprising an elongate article provided with at least three longitudinal grooves on its surface and an inserter comprising at least three prongs resting in said grooves and an insertion handle joined to said prongs.

16. A tampon and inserter combination comprising an elongate compressed absorbent tampon, a withdrawal string attached to said tampon, at least three longitudinal grooves in said tampon and an inserter comprising at least three flexible prongs resting in said grooves and a flexible insertion handle joined to said prongs.

* * * * *